(12) United States Patent
Shirotori et al.

(10) Patent No.: US 12,140,834 B2
(45) Date of Patent: Nov. 12, 2024

(54) OPTICAL SYSTEM WITH BLUE LIGHT ABSORBING LAYER

(71) Applicant: 3M INNOVATIVE PROPERTIES COMPANY, St. Paul, MN (US)

(72) Inventors: Hideaki Shirotori, Yokohama (JP); Naota Sugiyama, Tokyo (JP); Taiki Ihara, Tokyo (JP); Hiroki Hayashi, Sagamihara (JP)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 17/701,766

(22) Filed: Mar. 23, 2022

(65) Prior Publication Data

US 2022/0308391 A1 Sep. 29, 2022

Related U.S. Application Data

(60) Provisional application No. 63/200,764, filed on Mar. 26, 2021.

(51) Int. Cl.
*G02F 1/1335* (2006.01)
*C07D 249/20* (2006.01)

(52) U.S. Cl.
CPC ..... *G02F 1/133514* (2013.01); *C07D 249/20* (2013.01); *G02F 1/133536* (2013.01); *G02F 1/133553* (2013.01); *G02F 2202/10* (2013.01)

(58) Field of Classification Search
CPC ......... G02F 1/133514; G02F 1/133536; G02F 1/133553; G02F 2202/10
USPC ...................................................... 349/61–63
See application file for complete search history.

(56) References Cited

U.S. PATENT DOCUMENTS

| 9,063,349 | B2 | 6/2015 | Ishak | |
|---|---|---|---|---|
| 9,798,163 | B2* | 10/2017 | Ishak | G02B 1/11 |
| 11,126,033 | B2* | 9/2021 | Garbar | G02F 1/133536 |
| 2017/0090244 | A1* | 3/2017 | Jiang | H01L 29/78633 |
| 2019/0391308 | A1* | 12/2019 | Nomura | G02B 1/11 |
| 2021/0139776 | A1* | 5/2021 | Kim | C09K 11/71 |

FOREIGN PATENT DOCUMENTS

| CN | 104848093 | 8/2015 |
|---|---|---|
| CN | 104849789 | 8/2015 |
| CN | 205450322 | 8/2016 |
| CN | 205750207 | 11/2016 |
| CN | 206489288 | 9/2017 |
| CN | 107561608 | 1/2018 |
| JP | 2014-199285 | 10/2014 |
| JP | 2015-079139 | 4/2015 |
| JP | 2015-194553 | 11/2015 |
| JP | 2017-003884 | 1/2017 |

(Continued)

*Primary Examiner* — Charles S Chang
(74) *Attorney, Agent, or Firm* — Jonathan L. Tolstedt

(57) ABSTRACT

An optical system includes a display, a backlight configured to emit at least a light in a first wavelength range extending between about 400 nm and about 500 nm, and an optical film disposed adjacent the backlight and configured to absorb a light in a second wavelength range extending between about 415 nm to about 455 nm, wherein a ratio of the light in the second wavelength range transmitted by the optical film to the light in the first wavelength range transmitted by the optical film is less than or equal to 50%.

13 Claims, 6 Drawing Sheets

(56) References Cited

FOREIGN PATENT DOCUMENTS

| | | |
|---|---|---|
| JP | 2017-142412 | 8/2017 |
| JP | 2018-069573 | 5/2018 |
| JP | 2018-177696 | 11/2018 |
| JP | 6486128 | 3/2019 |
| WO | WO 2014-155787 | 10/2014 |
| WO | WO 2016-205260 | 12/2016 |
| WO | WO 2018-021485 | 2/2018 |
| WO | WO 2018-143167 | 8/2018 |
| WO | WO 2018-207843 | 11/2018 |
| WO | WO 2019-127710 | 7/2019 |

\* cited by examiner

OPTICAL SYSTEM WITH BLUE LIGHT ABSORBING LAYER

This application claims the benefit of U.S. Provisional Application No. 63/200,764, filed Mar. 26, 2021, the disclosure of which is incorporated by reference in its entirety herein.

SUMMARY

In some aspects of the present description, an optical system is provided, the optical system including a display, a backlight configured to emit at least a light in a first wavelength range extending between about 400 nm and about 500 nm, and an optical film disposed adjacent the backlight and configured to absorb a light in a second wavelength range extending between about 415 nm to about 455 nm. A ratio of the light in the second wavelength range transmitted by the optical film to the light in the first wavelength range transmitted by the optical film is less than or equal to 50%.

In some aspects of the present description, an optical system is provided, the optical system, including a liquid crystal display, a backlight configured to emit at least a light in a first wavelength range extending between about 400 nm and about 500 nm, and a reflective polarizer disposed between the backlight and the liquid crystal display. The reflective polarizer is configured to absorb a light in a second wavelength range extending between about 415 nm to about 455 nm. The light in the second wavelength range transmitted by the liquid crystal display is less than the light in the first wavelength range transmitted by the liquid crystal display.

DETAILED DESCRIPTION

Figure 1:
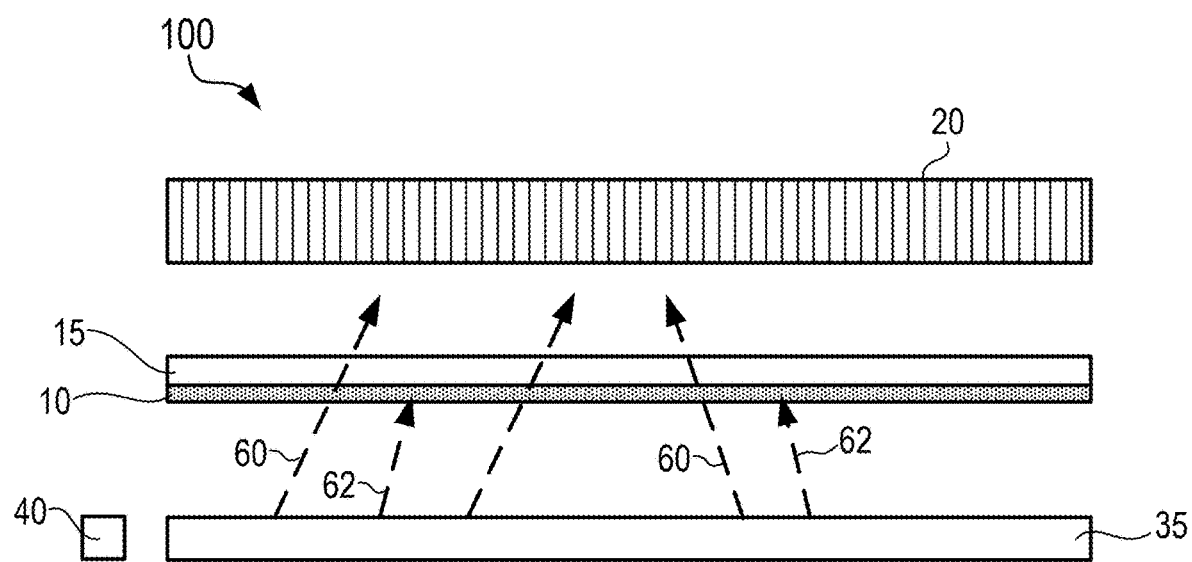
FIG. 1 is a side view of an optical system with reflective polarizer having a blue light absorbing layer, in accordance with an embodiment of the present description.

In the following description, reference is made to the accompanying drawings that form a part hereof and in which various embodiments are shown by way of illustration. The drawings are not necessarily to scale. It is to be understood that other embodiments are contemplated and may be made without departing from the scope or spirit of the present description. The following detailed description, therefore, is not to be taken in a limiting sense.

Some studies show that blue spectrum light (and, in particular, light between 415 nm and 455 nm) from a display (e.g., a liquid crystal display) may be harmful to the human eye. In some cases, the blue spectrum light may cause health issues including, but not limited to, dry, irritated eyes, trouble sleeping, blurred vision, reduced attention span, irritability, and difficulty concentrating. Standards have been developed by the American National Standards Institute (ANSI) and other commercial suppliers defining requirements for displays and other light sources that are safer for human eyes, but which also meet certain performance requirements. These requirements include, among other things, that the ratio of light in the range from 415 nm to 455 nm compared to the light in the range 400 nm to 500 nm must be less than 50%, and that the correlated color temperature (CCT) much be with the range of 5500 K and 7000 K (preferably above 6000 K).

Existing solutions include changing the formulation of the phosphor on light sources such as light-emitting diodes (LEDs) to reduce blue light, and placing a blue light absorbing film on the outside of a display. However, both of these solutions have their drawbacks. Changing the formulation of the phosphor on LEDs, for example, may create a noticeable drop in illumination efficiency. Blue light absorbing films placed on the outside of displays typically have a base layer (such as polyethylene terephthalate, or PET) which effects a transmittance drop and often causes a color shift into yellow wavelengths.

According to some aspects of the present description, an optical system includes a display (e.g., a liquid crystal display), a backlight, and an optical film disposed adjacent the backlight. In some embodiments, the backlight is configured to emit at least a light in a first wavelength range extending between about 400 nm and about 500 nm. In some embodiments, the optical film is configured to absorb a light in a second wavelength range extending between about 415 nm to about 455 nm (e.g., a blue wavelength range).

In some embodiments, the optical film may be disposed between the backlight and the display (e.g., as a standalone layer or as a layer in an optical stack, where the optical film may not be directly in contact with either the display or the backlight). In such embodiments, the optical film may be at least one of a reflective polarizer, a light redirecting film, and an optically diffusive film.

In other embodiments, the optical film may be disposed on a side of the backlight away from the display, such that the backlight is disposed between the optical film and the display. In such embodiments, the optical film may be an optical reflector, or a layer in an optically reflecting layer.

In some embodiments, a ratio of the light in the second wavelength range transmitted by the optical film to the light in the first wavelength range transmitted by the optical film is less than or equal to 50%. Stated another way, if T1 represents the percentage of light transmitted in the second wavelength range (e.g., between about 415 nm and about 455 nm), and T2 represents the percentage of light transmitted in the first wavelength range (e.g., the total light transmitted between about 400 nm and about 500 nm), then T1/T2 may be less than or equal to 0.5 (i.e., 50%).

In some embodiments, the optical film may include a light absorbing layer configured to absorb the light in the second wavelength range (e.g., a separate film or a coating applied to the optical film). In some embodiments, the light absorbing layer may include benzotriazole. In some embodiments, the light absorbing layer may further include $SiO_2$ (e.g., as a durability additive).

According to some aspects of the present description, an optical system includes a liquid crystal display (LCD), a backlight configured to emit at least a light in a first wavelength range extending between about 400 nm and about 500 nm, and a reflective polarizer disposed between the backlight and the liquid crystal display and configured to absorb a light in a second wavelength range extending between about 415 nm to about 455 nm. In some embodiments, the light in the second wavelength range transmitted by the liquid crystal display is less than the light in the first wavelength range transmitted by the liquid crystal display. For example, in some embodiments, the ratio of the light in the second wavelength range transmitted by the liquid crystal display to the light in the first wavelength range transmitted by the liquid crystal display is less than or equal to about 50%. Stated another way, if T1 represents the percentage of light transmitted in the second wavelength range (e.g., between about 415 nm and about 455 nm), and T2 represents the percentage of light transmitted in the first wavelength range (e.g., the total light transmitted between about 400 nm and about 500 nm), then T1/T2 may be less than or equal to 0.5 (i.e., 50%).

In some embodiments, the optical system may include one or more additional layers, including one or more of a light redirecting film (e.g., prism film or light collimating film), an optically diffusive film, and an optical reflector. In some embodiments, the reflective polarizer may include a light absorbing layer (e.g., a separate film or coating) configured to absorb the light in the second wavelength range. In some embodiments, the light absorbing layer may include benzotriazole. In such embodiments, the light absorbing layer may further include SiO$_2$ (e.g., to add durability to the light absorbing layer).

Turning now to the figures, FIG. 1 is a side view of an optical system with reflective polarizer having a blue light absorbing layer, according to the present description. In some embodiments, an optical system 100 includes a display (e.g., a liquid crystal display), a light source 40 (e.g., a light-emitting diode 40 and lightguide 35), and a reflective polarizer 15. In some embodiments, the reflective polarizer 15 may be disposed between the light source 40 (including, if applicable, lightguide 35) and display 20. In some embodiments, the reflective polarizer 15 may be configured to absorb light at least in a blue wavelength range (e.g., light between about 415 nm and about 455 nm). In some embodiments, reflective polarizer 15 may further include a light absorbing layer 10 disposed on and substantially coextensive with reflective polarizer 15, and it is light absorbing layer 10 which is configured to absorb light in the blue wavelength range. In some embodiments, light absorbing layer 10 may be a coating or an optical film. In some embodiments, light absorbing layer 10 may include benzotriazole. In such embodiments, light absorbing layer 10 may further include SiO$_2$, or any appropriate material to add durability to light absorbing layer 10.

In some embodiments, light source 40 is configured to emit at least a first light 60 in a first wavelength range extending between about 400 nm and about 500 nm. In some embodiments, first light 60 may include second light 62 in a second wavelength range extending between about 415 nm and about 455 nm (i.e., light in the second wavelength range may include those wavelengths of blue light which are considered to be the most harmful to humans). Light absorbing layer 10 may at least partially absorb light 62 (i.e., light in the second wavelength range), while light in the first wavelength range but not included in the second wavelength range may have a higher transmittance through light absorbing layer 10. In some embodiments, if T1 represents the percentage of light transmitted in the second wavelength range, and T2 represents the percentage of light transmitted in the first wavelength range, then T1/T2 may be less than or equal to 0.5 (i.e., 50%).

Figure 2:
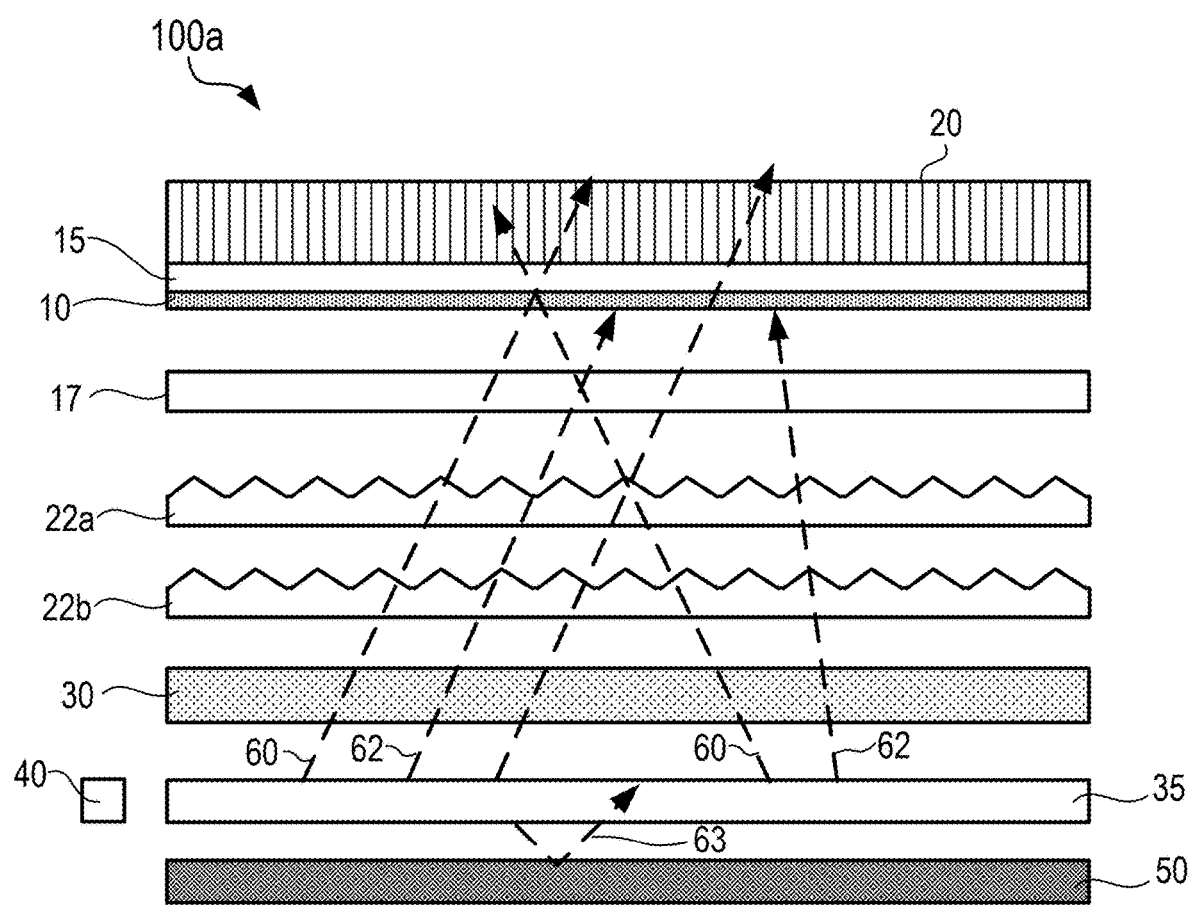
FIG. 2 is a side view of an alternate optical system with an optical film having a blue light absorbing layer, in accordance with an embodiment of the present description.

FIG. 2 is a side view of an alternate optical system 100a with an optical film having a blue light absorbing layer and other additional layers, according to one embodiment of the present description. Optical system 100a includes a display 20 (e.g., a liquid crystal display), a reflective polarizer 15 including light absorbing layer 10, and light source 40 and lightguide 35. In some embodiments, reflective polarizer 15 and light absorbing layer 10 are adjacent each other and substantially coextensive, and disposed between light source 40 and lightguide 35. In some embodiments, reflective polarizer 15 and light absorbing layer 10 may be of a unitary construction (i.e., integrated into a single film or layer rather than separate layers). In some embodiments, for example, light absorbing layer 10 may be a coating on reflective polarizer 15. In other embodiments, light absorbing layer 10 may be integral to reflective polarizer 15 (e.g., an additive to reflective polarizer 15).

In some embodiments, optical system 100a may further include additional layers or components, including one or more of a cover sheet 17, light redirecting layer(s) 22a/22b, an optical diffuser layer 30, and an optical reflector layer 50. As with optical system 100 of FIG. 1, the light source 40 may be configured to emit at least a first light 60 in a first wavelength range extending between about 400 nm and about 500 nm (e.g., light emitted by light source 40 into lightguide 35 may be redirected by lightguide 35 toward the reflective polarizer 15, and a portion of light 63 may be directed toward, and reflected by, reflective layer 50). Second light 62 may be a subset of first light 60 limited to a second wavelength range extending between about 415 nm to about 455 nm. In some embodiments, either reflective polarizer 15, light absorbing layer 10, or a combination thereof may absorb at least a portion of light in a second wavelength range.

Figure 3:
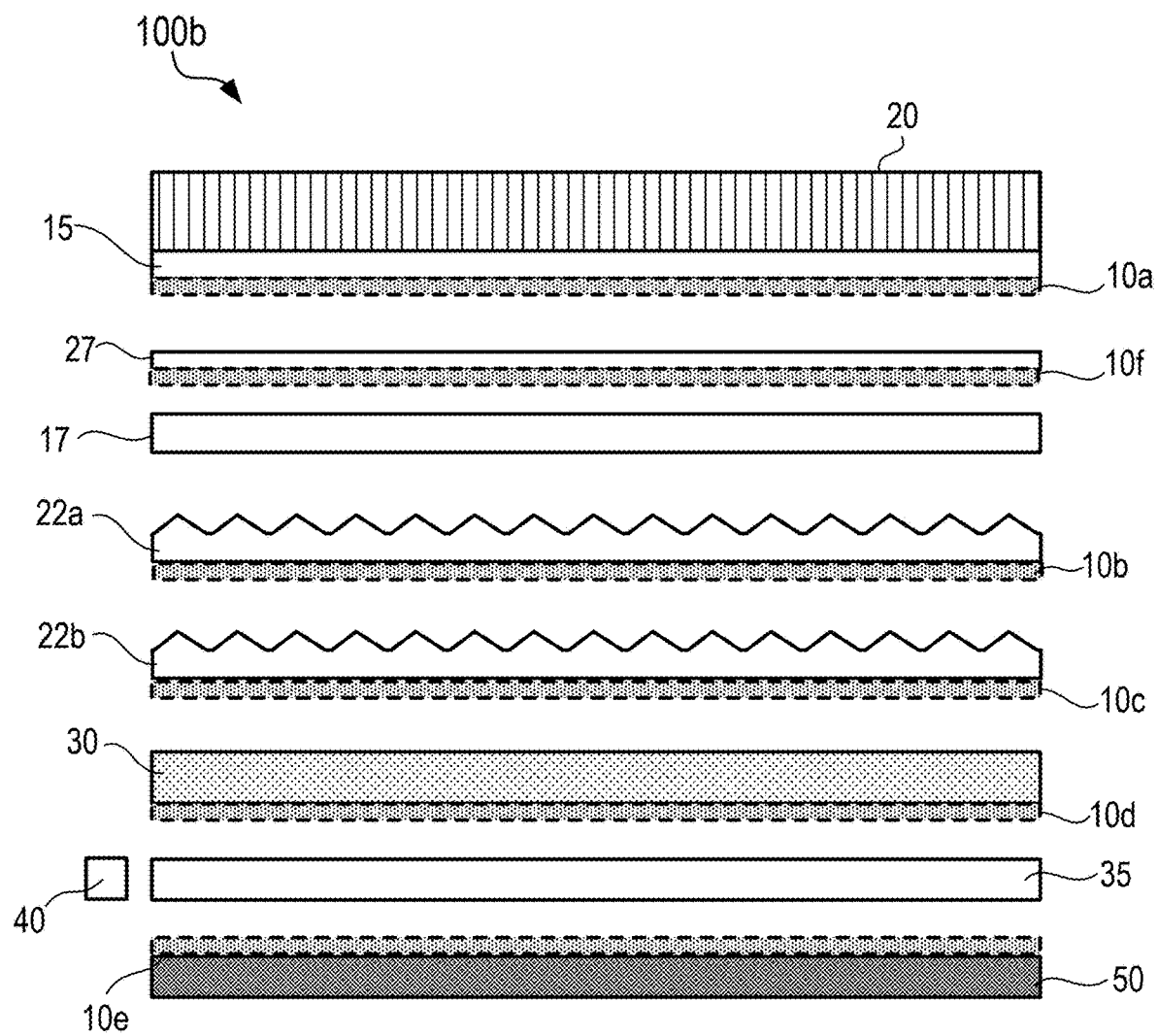
FIG. 3 is a side view of an optical system showing possible locations for a blue light absorbing layer, in accordance with an embodiment of the present description.

In some embodiments of the optical system 100a, light absorbing layer 10 may be disposed at a location in optical system 100a as an alternate to, or in addition to, the reflective polarizer 15. FIG. 3 provides an example of such an optical system 100b. Optical system 100b is similar to the embodiment of optical system 100a of FIG. 2 but shows additional locations where the light absorbing layer 10 may be placed. Various locations of light absorbing layer 10 are indicated in FIG. 3 using the reference designators 10a through 10f. In some embodiments, light absorbing layer 10 may be disposed in one of the locations 10a-10f, or in any appropriate combinations of locations 10a-10f (i.e., in two or more of the locations). It should be noted that locations 10a-10f are not intended to be limiting, and other locations (e.g., above the display 20, on an opposing side of the film from any of those shown in FIG. 3, etc.) may be used consistently with the present description.

As described elsewhere herein, in some embodiments, the light absorbing layer 10 may be disposed on or near to reflective polarizer 15 (light absorbing layer 10a). In some embodiments, the light absorbing layer 10 may be disposed on or near one or more light redirecting films (e.g., prism films) 22a/22b (light absorbing layer 10b/10c). In some embodiments, the light absorbing layer 10 may be disposed on or near optical diffuser layer 30 (light absorbing layer 10d). In some embodiments, the light absorbing layer 10 may be disposed on or near optical reflector layer 50 (light absorbing layer 10e). In some embodiments, the light absorbing layer 10 may be disposed on or near an additional layer 27 (light absorbing layer 100, such as an optically transparent substrate 27 such as polyethylene terephthalate, or PET.

Figure 4:
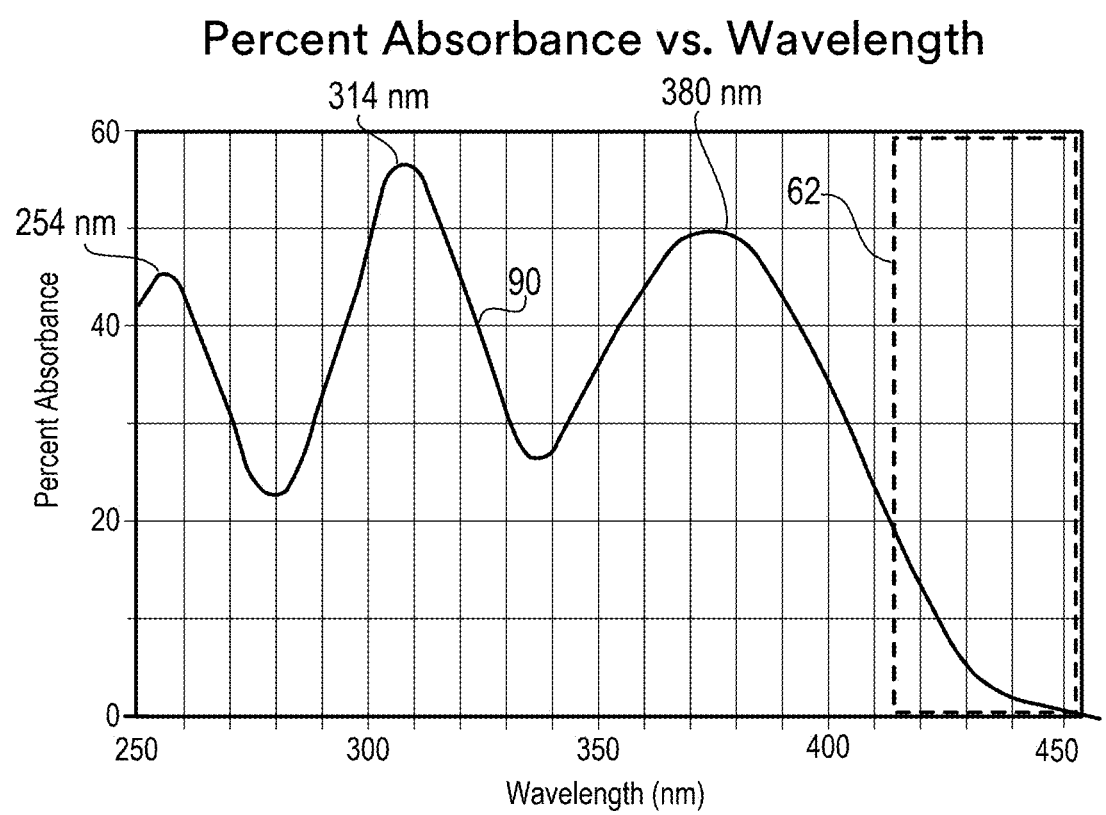
FIG. 4 is a plot of percent optical absorbance vs. wavelength for a blue light absorbing layer, in accordance with an embodiment of the present description.

FIG. 4 is a representative plot 90 showing a typical percent optical absorbance vs. wavelength for one embodiment of a blue light absorbing layer, according to the present description. For the purposes of this specification, optical absorbance is defined as a measure of the amount of light (which may be of a specific wavelength or range of wavelengths) that is absorbed when passing through a substance. Plot 90 shows that, for this embodiment of the blue light absorbing layer (e.g., layer 10 in FIG. 1), at least a portion of the light with wavelengths in both the ultraviolent and blue light wavelengths is absorbed by the layer. Plot 90 shows at least a portion of light 62 between 415 nm and 455 nm (i.e., the wavelengths of light considered to be most deleterious to humans) is absorbed, and that light above about 455 nm is substantially not absorbed. The plot of FIG. 4 was created from the experimental steps described in the Examples section below.

EXAMPLES

The following section describes the synthesis and evaluation of a benzotriazole-based additive with ultraviolet and blue light absorbance. TABLE 1 provides a list of materials used in the preparation of the examples below.

TABLE 1

Material List

| Description | Type | Source |
| --- | --- | --- |
| 4-Amino-3-nitrobenzoic Acid | reagent | Tokyo Chemical Industry |
| Hydrazine Monohydrate | reagent | Tokyo Chemical Industry |
| 3-tert-butyl-4-hydroxyanisole | reagent | Tokyo Chemical Industry |
| hydroquinone | reagent | Fujifilm Wako Chemicals |
| thiourea dioxide | reagent | Fujifilm Wako Chemicals |
| sodium nitrite | reagent | Fujifilm Wako Chemicals |
| sodium carbonate | reagent | Fujifilm Wako Chemicals |
| sulfonic acid | reagent | Fujifilm Wako Chemicals |
| 2-propanol | solvent | Fujifilm Wako Chemicals |
| ethylacetate | solvent | Fujifilm Wako Chemicals |

Figure 5A:
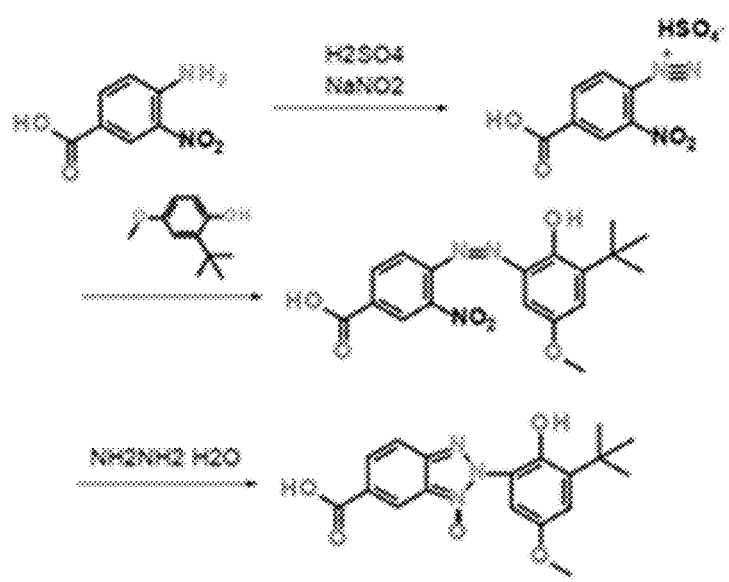
FIGS. 5A and 5B show the steps in the synthesis of a benzotriazole-based additive with ultraviolet and blue light absorbance, in accordance with an embodiment of the present description.
Figure 5B:
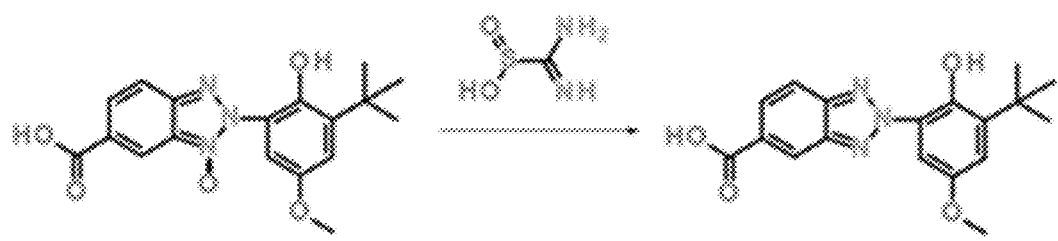

Synthesis: FIGS. 5A and 5B graphically depict the two-step process used in the synthesis process and described herein. In Step 1, 4-amino-3-nitrobenzoic acid (20.0 g, 110 mmol), water (150 mL), sodium carbonate (6.5 g, 61 mmol) were added into a 450 mL glass jar. A 36% aqueous solution of sodium nitrite (22.7 g, 118 mmol) was added to this suspension dropwise. Water (116.1 g) and 98% sulfonic acid (26.875 g, ~14.7 mL) were added into another 450 mL glass jar carefully. Then the glass jar was immersed into an ice bath. To the chilled sulfonic acid solution, the ocher suspension (FIG. 5A) was added dropwise to produce the diazonium compound. The mixture was stirred for 2 hours in the ice bath.

Into another three-neck 1000 mL flask were added 2-propanol (30 mL) and water (140 mL). Then 3-tert-butyl-4-hydroxyanisole (18.0 g, 100 mmol) was dissolved. The flask was immersed into an ice bath. To that hydroxyanisole solution, the iced diazonium aqueous solution (ocher) was added dropwise over 30 min to yield a purple suspension. The suspension was stirred for 2-3 hours at ice bath temperature and then at room temperature overnight.

The following day, a 32% aqueous solution of sodium hydroxide (27.8 g) and 2-propanol (200 mL), ethylacetate and brine were added. The organic phase with precipitates were collected, and the solvent was evaporated.

A solution of water (200 mL), 32% aqueous solution of sodium hydroxide (30.0 g) and hydroquinone (0.40 g) was prepared. Into a three-neck flask were added the azo compound and the above solution. The solution displayed dark blue. The dark blue solution was warmed up to 40° C. and stirred for 90 minutes. To that solution was added a 60% aqueous solution of hydrazine monohydrate (6.0 g) dropwise via syringe over 1 hour. The reaction solution was stirred at 40° C. for another 2 hours. After that, the solution was cooled to room temperature and 62.5% sulfonic acid was added to adjust pH to 2-4 using litmus paper. During that, the solid was precipitated. The ocher precipitates were collected by vacuum filtration with water rinsing and dried under vacuum at 80° C. for 1 hour.

Yield: 12.83 g (ocher solid, "Solid A").

FIG. 5B depicts the details of Step 2. Into a two-neck 200 mL flask equipped with a condenser were added the ocher solid "Solid A" (11.8 g), 2-propanol (50 mL), water (50 mL) and a 32% aqueous solution of sodium hydroxide (12.0 g). The dark red solution was warmed up to 70° C., then thiourea dioxide (6.0 g) was added portion-wise over 2 hours. The solution was stirred at 70° C. for another 2 hours at 70° C., in which the color changed from dark red, to wine red, then to orange, and finally to yellow. After cooling to room temperature and stopping stirring, the solution was clearly separated into organic phase and water phase. The below-water phase was removed by Pasteur pipette.

Into the organic phase with stirring, 62.5% sulfonic acid was added to adjust the pH to 2-4 using litmus paper. During that, the yellow solid was precipitated. The clear yellow precipitates were collected by vacuum filtration with water rinsing and dried under vacuum at 80° C. for 2 hours.

Yield: 6.54 g (clear yellow solid, "Solid B").

The UV-vis absorption spectrum of the synthesized compound was measured at 10 ppm in chloroform. The synthesized compound (Solid B) showed ultraviolet to blue light absorption (up to 450 nm) with the characteristic peaks at about 254 nm, 314 nm, and 380 nm, as shown in FIG. 4.

Evaluation: Next, samples were prepared using the following steps. A reflective polarizer film (3M's APF-V4 film) was prepared as a base film. The materials shown in TABLE 2 below were used to synthesize the coating material for use on the base films. Synthesized compound Solid B described above was used in the evaluation performed.

TABLE 2

Material List for UV Curable Coating

| Abbreviation | Description | Type | Source |
| --- | --- | --- | --- |
| CN991NS | aliphatic polyester based urethane diacrylate oligomer | UV curable diacrylate | Sartomer Arkema Group |
| SR502 | ethoxylated trimethylolpropane triacrylate | UV curable triacrylate | Sartomer Arkema Group |
| Viscoat 196 | 3,3,5-trimethylcyclohexyl-acrylate | UV curable monoacrylate | OSAKA ORGANIC CHEMICAL INDUSTRY LTD |
| Tegoflow425 | polyether siloxane polymer | flow and anti-crater additive | EVONIK |
| Irgacure184 | 1-hydroxycyclohexyl phenyl ketone | photoinitiator | BASF |
| MP-OH | 1-methoxy-2-propanol | solvent | |
| APFV4 | APFV4 | substrate | 3M DMSD |

Figure 6:
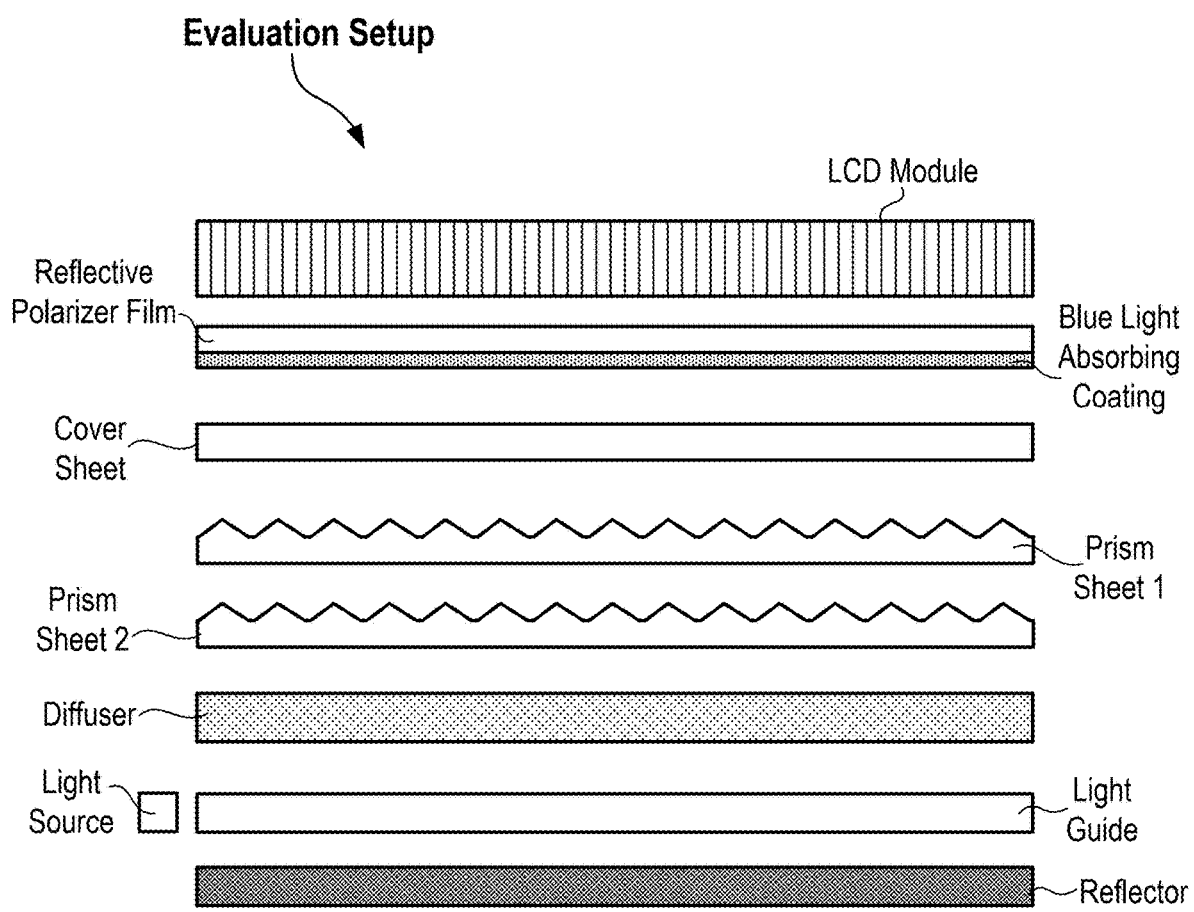
FIG. 6 shows the evaluation setup used to test a series of prepared sample films, in accordance with an embodiment of the present description.

0.90 grams of aliphatic polyester based urethane diacrylate oligomer "CN991NS", 0.90 grams of ethoxylated trimethylolpropane triacrylate "SR502", 0.45 grams of 3,3,5-trimethylcyclohexylacrylate "Viscoat196" were mixed. 0.068 gram of 1-hydroxycyclohexyl phenyl ketone "Irgacure 184" as the photoinitiator, 0.0045 grams of polyether siloxane polymer "BYK Tegoflow425", 0.068 grams of benzotriazole type additive "Solid B" which were obtained above were added to the mixture. Then 2.75 grams of 1-methoxy-2-propanol were added to the mixture. The precursor solution was provided. Advanced polarizer film "APF V4" with a thickness of 16 micrometer was used as a substrate. The coating layer with thickness of 9.0 um was formed by Mayer Rod #20 using the precursor solution. After drying for 5 min at 60° C. in the air. The coated substrate was passed 2 times into UV irradiator (H-bulb of Fusion UV System Inc. DRS model) under nitrogen gas. During irradiation, 900 mJ/cm2, 700 mW/cm2 of ultraviolet (UV-A) was totally irradiated on the coated surface. The prepared (coated) films were evaluated using the following procedure. A 13.4" LCD module utilizing Dell XPS13 2017 year model was prepared as a test bed for the sample films. The configuration of the LCD test bed used in testing the samples is shown in FIG. 6. Each of the sample films was assembled into the backlight module of the LCD test bed. The luminance, color temperature, and a blue light ratio (as explained below) of the resulting LCD test bed were measured. The optical performance goals of the LCD test bed using the sample films include a luminance target compared to a reference film (with no coating) of 99%, a color temperature of over 6000° K., and a ratio of light in the range from 415 nm to 455 nm compared to the light in the range from 400 nm to 500 nm should be less than 50% ("blue light ratio" mentioned above).

All sample films prepared using the synthesized compound Solid B as described above met or exceeded positively the requirements described above.

Terms such as "about" will be understood in the context in which they are used and described in the present description by one of ordinary skill in the art. If the use of "about" as applied to quantities expressing feature sizes, amounts, and physical properties is not otherwise clear to one of ordinary skill in the art in the context in which it is used and described in the present description, "about" will be understood to mean within 10 percent of the specified value. A quantity given as about a specified value can be precisely the specified value. For example, if it is not otherwise clear to one of ordinary skill in the art in the context in which it is used and described in the present description, a quantity having a value of about 1, means that the quantity has a value between 0.9 and 1.1, and that the value could be 1.

Terms such as "substantially" will be understood in the context in which they are used and described in the present description by one of ordinary skill in the art. If the use of "substantially equal" is not otherwise clear to one of ordinary skill in the art in the context in which it is used and described in the present description, "substantially equal" will mean about equal where about is as described above. If the use of "substantially parallel" is not otherwise clear to one of ordinary skill in the art in the context in which it is used and described in the present description, "substantially parallel" will mean within 30 degrees of parallel. Directions or surfaces described as substantially parallel to one another may, in some embodiments, be within 20 degrees, or within 10 degrees of parallel, or may be parallel or nominally parallel. If the use of "substantially aligned" is not otherwise clear to one of ordinary skill in the art in the context in which it is used and described in the present description, "substantially aligned" will mean aligned to within 20% of a width of the objects being aligned. Objects described as substantially aligned may, in some embodiments, be aligned to within 10% or to within 5% of a width of the objects being aligned.

All references, patents, and patent applications referenced in the foregoing are hereby incorporated herein by reference in their entirety in a consistent manner. In the event of inconsistencies or contradictions between portions of the incorporated references and this application, the information in the preceding description shall control.

Descriptions for elements in figures should be understood to apply equally to corresponding elements in other figures, unless indicated otherwise. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed is:

1. An optical system, comprising:
   a liquid crystal display;
   a backlight configured to emit at least a light in a first wavelength range extending between about 400 nm and about 500 nm; and
   an optical film disposed adjacent the backlight and configured to absorb a light in a second wavelength range extending between about 415 nm to about 455 nm;
   wherein a ratio of the light in the second wavelength range transmitted by the optical film to the light in the first wavelength range transmitted by the optical film is less than or equal to 50%; and wherein at least 90% of the light having wavelengths between 455 nm to 500 nm is transmitted by the optical film.

2. The optical system of claim 1, wherein the optical film further comprises a light absorbing layer configured to absorb the light in the second wavelength range.

3. The optical system of claim 2, wherein the light absorbing layer comprises benzotriazole.

4. The optical system of claim 3, wherein the light absorbing layer further comprises $SiO_2$.

5. The optical system of claim 1, wherein the optical film is disposed between the backlight and the liquid crystal display and comprises at least one of a reflective polarizer, a light redirecting film, and an optically diffusive film.

6. The optical system of claim 1, wherein the backlight is disposed between the liquid crystal display and the optical film, and the optical film comprises an optical reflector.

7. An optical system, comprising:
   a liquid crystal display;
   a backlight configured to emit at least a light in a first wavelength range extending between about 400 nm and about 500 nm; and
   a reflective polarizer disposed between the backlight and the liquid crystal display and configured to absorb a light in a second wavelength range extending between about 415 nm to about 455 nm;
   wherein a ratio of the light in the second wavelength range transmitted by the liquid crystal display to the light in the first wavelength range transmitted by the liquid crystal display is less than or equal to about 50%; and wherein at least 90% of the light having wavelengths between 455 nm to 500 nm is transmitted by the optical film.

8. The optical system of claim 7, further comprising one or more of a light redirecting film, an optically diffusive film, and an optical reflector.

9. The optical system of claim 7, wherein the reflective polarizer further comprises a light absorbing layer configured to absorb the light in the second wavelength range.

10. The optical system of claim 9, wherein the light absorbing layer comprises benzotriazole.

11. The optical system of claim 10, wherein the light absorbing layer further comprises $SiO_2$.

12. The optical system of claim 9, wherein the light absorbing layer comprises a light absorbing coating.

13. The optical system of claim 10, wherein the light absorbing layer comprises a light absorbing film.

* * * * *